US007098246B2

(12) United States Patent
Geelings et al.

(10) Patent No.: US 7,098,246 B2
(45) Date of Patent: Aug. 29, 2006

(54) NATURAL COMPOUNDS AND THEIR DERIVATIVES FOR THE PREVENTION AND TREATMENT OF CARDIOVASCULAR, HEPATIC AND RENAL DISEASES AND FOR COSMETIC APPLICATIONS

(75) Inventors: Arjan Geelings, Granada (ES); Eduardo Lopez-Huertas Leon, Granada (ES); Juan Carlos Morales Sanchez, Granada (ES); Julio Boza Puerta, Granada (ES); Jesús Jimenez Lopez, Granada (ES)

(73) Assignee: Puleva Biotech, S.A., Granada (ES)

( * ) Notice: Subject to any disclaimer, the term of this patent is extended or adjusted under 35 U.S.C. 154(b) by 64 days.

(21) Appl. No.: 10/406,792

(22) Filed: Apr. 3, 2003

(65) Prior Publication Data

US 2003/0225160 A1 Dec. 4, 2003

(30) Foreign Application Priority Data

Apr. 3, 2002 (ES) ................................. 200200772

(51) Int. Cl.
*A61K 31/23* (2006.01)
*C07C 57/00* (2006.01)
*A61Q 17/04* (2006.01)
*A23L 15/00* (2006.01)
*A23J 3/00* (2006.01)

(52) U.S. Cl. ........................ 514/552; 554/229; 424/60; 426/569; 426/581; 426/599; 426/603; 426/611

(58) Field of Classification Search ................ 514/549, 514/552; 554/223, 229; 424/60; 426/569, 426/581, 599, 603, 611
See application file for complete search history.

(56) References Cited

FOREIGN PATENT DOCUMENTS

WO    WO 01/76579    * 10/2001

OTHER PUBLICATIONS

Owen et al, the antioxidant/anticancer potential of phenolic compounds isolated from olive oil, Jun. 2000, European Journal of Cancer, vol. 36, No. 10, p. 1235-1240.*

* cited by examiner

*Primary Examiner*—Taylor Victor Oh
(74) *Attorney, Agent, or Firm*—Katten Muchin Rosenman LLP

(57) ABSTRACT

The present invention refers to the use of phenolic compounds and their derivatives represented by formula I wherein $R_1$ and $R_2$ are selected from among: OH, OCOalkyl, or OCOalkenyl, and $R_3$ is either H, OH, OCOalkyl or OCOalkenyl, wherein the alkyl or alkenyl chains present from 2 to 22 carbon atoms and wherein at least one OCOalkyl or OCOalkenyl group is present in the structure, for the prevention and treatment of cardiovascular, hepatic or renal diseases, as well as to their cosmetic applications, to compositions that include these compounds and to some novel phenolic compounds and derivatives.

9 Claims, 2 Drawing Sheets

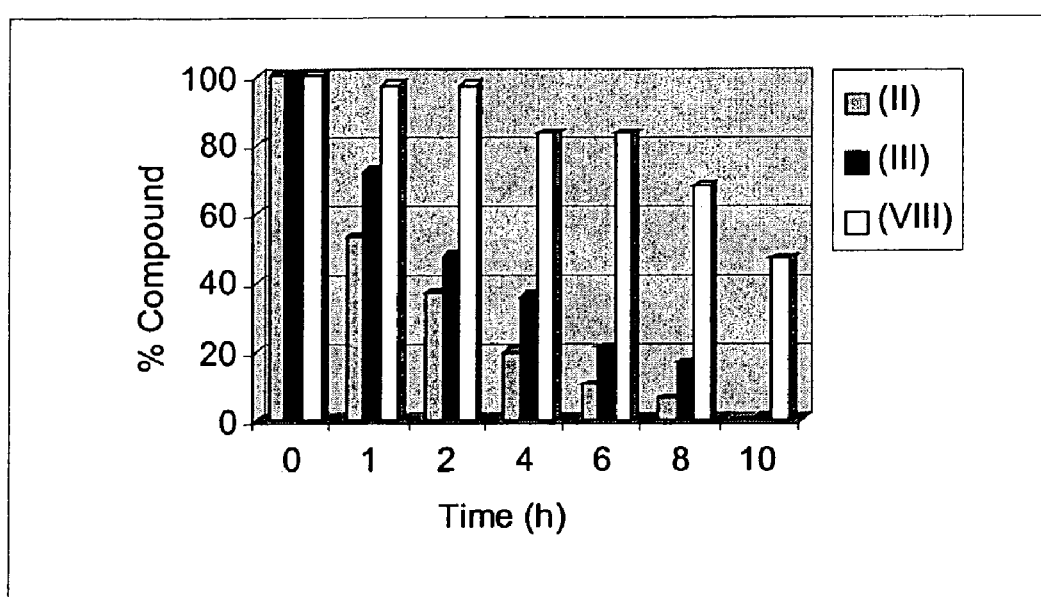
Figure I

Figure II
Mean plasma levels of hydroxytyrosol and vanillic acid detected after administration of an aqueous solution of hydroxytyrosol (2.5 mg/Kg weight).
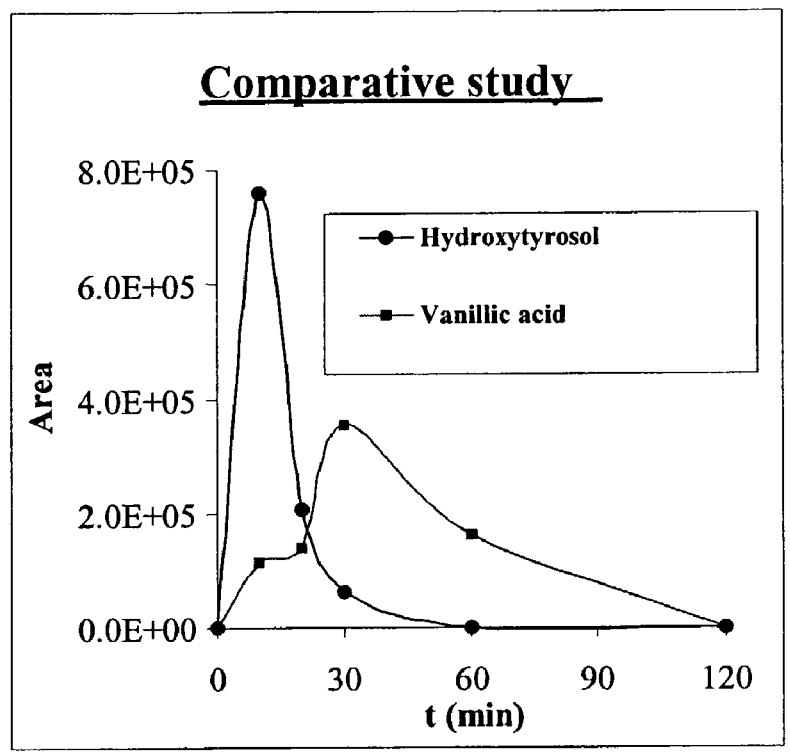

NATURAL COMPOUNDS AND THEIR DERIVATIVES FOR THE PREVENTION AND TREATMENT OF CARDIOVASCULAR, HEPATIC AND RENAL DISEASES AND FOR COSMETIC APPLICATIONS

FIELD OF THE INVENTION

The present invention refers to the use of phenolic compounds and their derivatives for the prevention and treatment of cardiovascular, hepatic and renal diseases, as well as to their cosmetic applications, to compositions that include these compounds and to some novel phenolic compounds and derivatives.

BACKGROUND OF THE INVENTION

Cardiovascular diseases are the first cause of death in developing countries. One of the non-genetic risk factors associated with the development of cardiovascular disease is diet. It has been shown that the incidence of these diseases is directly related to the presence of high blood cholesterol levels that can be caused by a diet with high cholesterol and saturated fat contents.

On the other hand, many studies have shown that oxidation or modification of low density lipoproteins (LDL) triggers the whole atherosclerotic process, in which endothelial activation and activated oxygen species play an important role. Epidemiological studies indicate that the Mediterranean diet is associated with a low incidence of cardiovascular diseases. The most common components of this diet include fruit and vegetables and also olive oil as the main source of fats, all products rich in antioxidants. Results from in vivo and in vitro studies show that antioxidants present in food can counteract the harmful effects of free radicals, preventing LDL oxidation and, therefore, also the atherosclerotic process.

Oxidative stress and the generation of free radicals also play an important part in hepatic and renal diseases, due to the high presence of oxygen in these organs, as well as in the trigger of the inflammatory processes in numerous situations. For this reason, antioxidants in the diet can be crucial to prevent this type of diseases.

Epidemiological studies have demonstrated that UV radiation is the main risk factor in skin cancer. The skin has a defence system to protect against reactive oxygen species produced after exposure to UV radiation, mainly via the enzymatic activities of superoxide dismutase and glutathion peroxidase. A reduction in this defence system, more specifically, in intracellular glutathion levels, produces an increase in the pigmentation, ageing of the skin, induction of apoptosis and can, finally, lead to skin cancer. Hence, supplementation with antioxidants (e.g. vitamin E) has been shown to reverse the situation of oxidative stress induced by UV radiation in human fibroblasts.

Olive oil is a healthy food product rich in oleic acid and antioxidants. Tyrosol and hydroxytyrosol are phenolic compounds obtained from the olive, with a strong antioxidant capacity that has been disclosed both in vivo and in vitro. The possible favorable role of tyrosol and hydroxytyrosol in cardiovascular diseases has been disclosed by some authors who have shown that these compounds reduce the susceptibility of LDL lipoproteins to the in vitro and in vivo oxidation (Masella et al. 2001, Lipids, 36, 1195–1202). It has also been suggested that hydroxytyrosol could reduce lipidic peroxidation in hepatic microsomes in animal studies and that the phenolic antioxidant compounds present in olive oil (tyrosol and hydroxytyrosol) could have a potent anti-inflammatory effect.

Tyrosol and hydroxytyrosol are easily oxidizable and, therefore, the use thereof in the form of olive extracts can result in an important proportion of the tyrosol and the hydroxytyrosol being oxidised in the food matrix, which would prevent oxidation of the food. However, both of these compounds would be degraded before entering the organism. It is, therefore, highly beneficial for tyrosol and hydroxytyrosol to reach the organism intact and to exert their strong antioxidant activity therein.

Olive extracts that contain tyrosol or hydroxytyrosol are polar fractions highly soluble in the aqueous phase. A process that would increase the solubility of the antioxidant in an oily phase would be of considerable interest for the food industry. The solubility of tyrosol and hydroxytyrosol can be increased by adding fatty acid chains. In this case, fatty acids can be used that also have beneficial effects on the type of diseases treated in this invention.

Diets have been disclosed such as the Mediterranean diet, which are rich in monounsaturated fats (MUFA) and poor in saturated fats, that have favorable effects on the cardiovascular risk profile (Feldman et al. 1999, Am. J. Clin. Nutr., 70, 953–4). It has been shown that MUFA intake reduces the triglyceride concentration in plasma in healthy volunteers with normal lipid levels (Kris-Etherton et al. 1999; Am. J. Clin. Nutr., 70, 1009–15).

It has also been reported that polyunsaturated fatty acids of the series n-3 (n-3 PUFA), mainly eicosapentanoic acid (EPA) and docosahexanoic acid (DHA), have beneficial effects on the cardiovascular system and on inflammatory processes. The activities disclosed for the n-3 PUFA include antiarrhythmic activity, inhibition of platelet aggregation and reduced plasma lipids and cholesterol levels (Connor et al. 2000, Am. J. Clin. Nutr., 71, 171S–5S).

SUMMARY OF THE INVENTION

The object of the invention is, therefore, to provide a series of compounds which, as mentioned previously, serve to prevent and to treat cardiovascular, hepatic, renal and inflammatory diseases which are protected against degradation, and which can easily be incorporated into nutritional products.

The present invention provides tyrosol and hydroxytyrosol molecules modified with at least one fatty acid via an ester type bond. These molecules are useful in the prevention and treatment of cardiovascular, hepatic and renal diseases, diabetes and inflammatory diseases and for cosmetic treatments using the antioxidant action of tyrosol and hydroxytyrosol since all these diseases present acute oxidative stress. Fatty acid esters of tyrosol and hydroxytyrosol are hydrolysed in vivo producing tyrosol and hydroxytyrosol, respectively, as well as the corresponding fatty acid. Hence, the resulting components can have antioxidant, anti-inflammatory and nutritional effects on the organism.

Moreover, and explained by the presence of the radical or radicals of the fatty acid(s) in the molecule, the esters of the present invention, on the one hand, present a degree of self-protection against their oxidative degradation, such that both tyrosol and hydroxytyrosol can reach the organism intact and, on the other hand, present different degrees of solubility in the aqueous phase and the fatty phase, that can be modulated in relation to the degree of esterification of the tyrosol or hydroxytyrosol and of the chosen esterifying fatty acid facilitating its incorporation into any kind of nutritional products. Finally, esterification of tyrosol or hydroxytyrosol provides an additional supplement of mono and polyunsaturated fatty acids, with a known beneficial effect for health.

DESCRIPTION OF FIGURES

FIG. 1 is a graph that shows the different stability to oxidation of compounds 2-(3,4-dihydroxyphenyl) ethyl acetate (III), 2-(3,4-diacetoxyphenyl) ethyl acetate (VII) and hydroxytyrosol (II) when they are incorporated in an oily food matrix.

FIG. 2 corresponds to a graph that shows a comparative study of the absorption after oral ingestion of hydroxytyrosol and vanillic acid, specifically, the mean plasma concentrations of hydroxytyrosol and vanillic acid detected after administration of an aqueous solution of hydroxytyrosol (2.5 mg/kg weight).

DETAILED DESCRIPTION OF THE INVENTION

The tyrosol and hydroxytyrosol derivatives disclosed in this invention have a common structure represented by formula (I), wherein at least one hydroxyl group must be modified with a fatty acid chain. The R groups vary within the formula generating different series of tyrosol and hydroxytyrosol derivatives. R1 and R2 groups can be a hydroxyl group or a hydroxyl group protected with a fatty acid chain via an ester type bond. The R3 group can be hydrogen (in the case of tyrosol or tyrosol esters), a hydroxyl group (in the case of hydroxytyrosol or hydroxytyrosol esters), or a hydroxyl group protected with a fatty acid chain via an ester type bond (in the case of hydroxytyrosol esters). The compounds can contain one, two or three fatty acid chains with a length ranging from 2 to 22 carbon atoms.

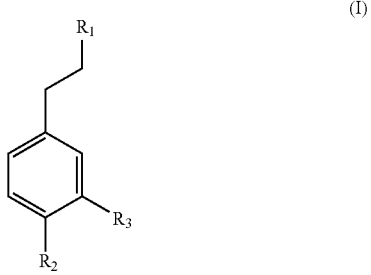

(I)

Note: Hydroxytyrosol or 2-(3,4-dihydroxyphenyl) ethanol has formula (II): R1, R2 and R3 are hydroxyl groups.

Tyrosol or 2-(4-hydroxyphenyl) ethanol has the formula (XV): R1 and R2 are hydroxyl groups and R3 is hydrogen.

A more practical illustration of some of the hydroxytyrosol derivatives included in the invention are:

(1) 2-(3,4-dihydroxyphenyl) ethyl acetate (III): R2 and R3 are hydroxyl groups and R1 is a hydroxyl group protected with acetic acid via an ester type bond.

(2) 2-(3,4-dihydroxyphenyl) ethyl stearate (IV): R2 and R3 are hydroxyl groups and R1 is a hydroxyl group protected with stearic acid via an ester type bond.

(3) 2-(3,4-dihydroxyphenyl) ethyl oleate (V): R2 and R3 are hydroxyl groups and R1 is a hydroxyl group protected with oleic acid via an ester type bond.

(4) 2-(3-stearyloxy-4-hydroxyphenyl) ethanol (VI): R1 and R3 are hydroxyl groups and R2 is a hydroxyl group protected with stearic acid via an ester type bond.

(5) 2-(4-stearyloxy-3-hydroxyphenyl) ethanol (VII): R1 and R2 are hydroxyl groups and R3 is a hydroxyl group protected with stearic acid via an ester type bond.

(6) 2-(3,4-diacetoxyphenyl) ethyl acetate (VIII): R1, R2 and R3 are hydroxyl groups protected with acetic acid via an ester type bond.

(7) 2-(3,4-distearyloxyphenyl) ethyl stearate (IX): R1, R2 and R3 are hydroxyl groups protected with stearic acid via an ester type bond.

(8) 2-(3,4-dioleyloxyphenyl) ethyl oleate (X): R1, R2 and R3 are hydroxyl groups protected with oleic acid via an ester type bond.

(9) 2-(3,4-dihydroxyphenyl) ethyl eicosapentanoate (XI): R2 and R3 are hydroxyl groups and R1 is a hydroxyl group protected with eicosapentanoic acid via an ester type bond.

(10) 2-(3,4-dihydroxyphenyl) ethyl docosahexanoate (XII): R2 and R3 are hydroxyl groups and R1 is a hydroxyl group protected with docosahexanoic acid via an ester type bond.

(11) 2-(3,4-dieicosapentanoyloxyphenyl) ethyl eicosapentanoate (XIII): R1, R2 and R3 are hydroxyl groups protected with eicosapentanoic acid via an ester type bond.

(12) 2-(3,4-didocosahexanoyloxyphenyl) ethyl docosahexanoate (XIV): R1, R2 and R3 are hydroxyl groups protected with docosahexanoic acid via an ester type bond.

(13) 2-(4-hydroxyphenyl) ethyl acetate (XVI): R2 is a hydroxyl group, R3 is hydrogen and R1 is a hydroxyl group protected with acetic acid via an ester type bond.

(14) 2-(4-hydroxyphenyl) ethyl stearate (XVII): R2 is a hydroxyl group, R3 is hydrogen and R1 is a hydroxyl group protected with stearic acid via an ester type bond.

(15) 2-(4-hydroxyphenyl) ethyl oleate (XVIII): R2 is a hydroxyl group, R3 is hydrogen and R1 is a hydroxyl group protected with oleic acid via an ester type bond.

(16) 2-(4-hydroxyphenyl) ethyl eicosapentanoate (XIX): R2 is a hydroxyl group, R3 is hydrogen and R1 is a hydroxyl group protected with eicosapentanoic acid via an ester type bond.

(17) 2-(4-hydroxyphenyl) ethyl docosahexanoate (XX): R2 is a hydroxyl group, R3 is hydrogen and R1 is a hydroxyl group protected with docosahexanoic acid via an ester type bond.

(18) 2-(4-acetoxyphenyl) ethyl acetate (XXI): R1 and R2 are hydroxyl groups protected with acetic acid via an ester type bond and R3 is a hydrogen.

(19) 2-(4-stearyloxyphenyl) ethyl stearate (XXII): R1 and R2 are hydroxyl groups protected with stearic acid via an ester type bond and R3 is a hydrogen.

(20) 2-(4-oleyloxyphenyl) ethyl oleate (XXIII): R1 and R2 are hydroxyl groups protected with oleic acid via an ester type bond and R3 is a hydrogen.

(21) 2-(4-eicosapentanoyloxyphenyl) ethyl eicosapentanoate (XXIV): R1 and R2 are hydroxyl groups protected with eicosapentanoic acid via an ester type bond and R3 is a hydrogen.

(22) 2-(4-docosahexanoyloxyphenyl) ethyl docosahexanoate (XXV): R1 and R2 are hydroxyl groups protected with docosahexanoic acid via an ester type bond and R3 is a hydrogen.

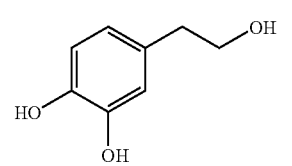

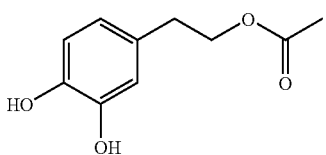

(III)

-continued
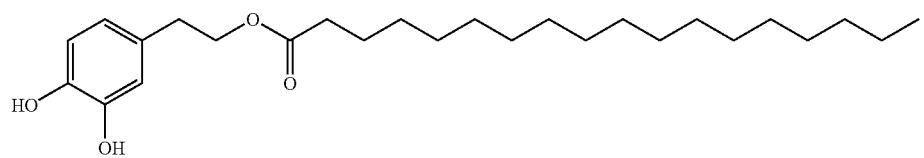
(IV)
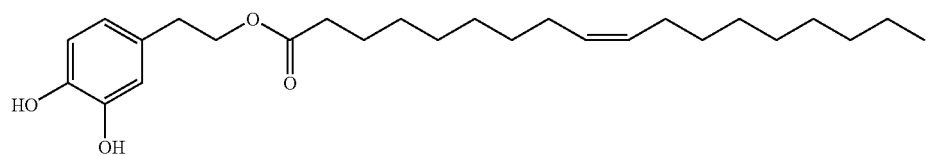
(V)
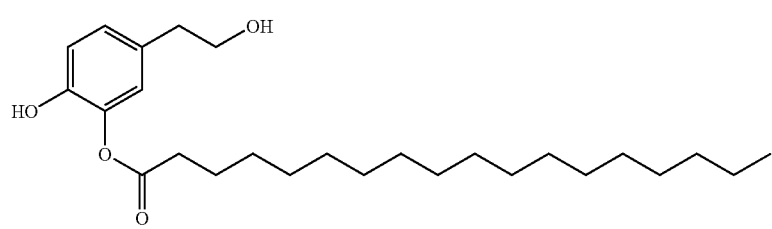
(VI)
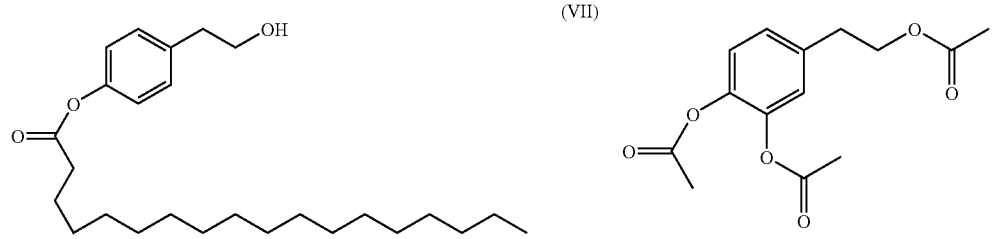
(VII) (VIII)
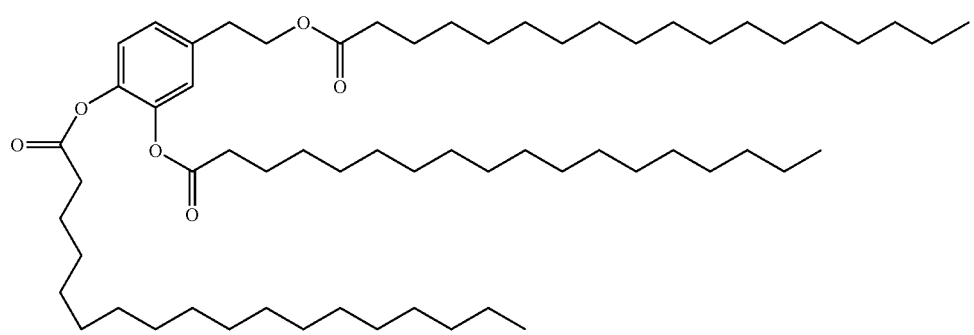
(IX)
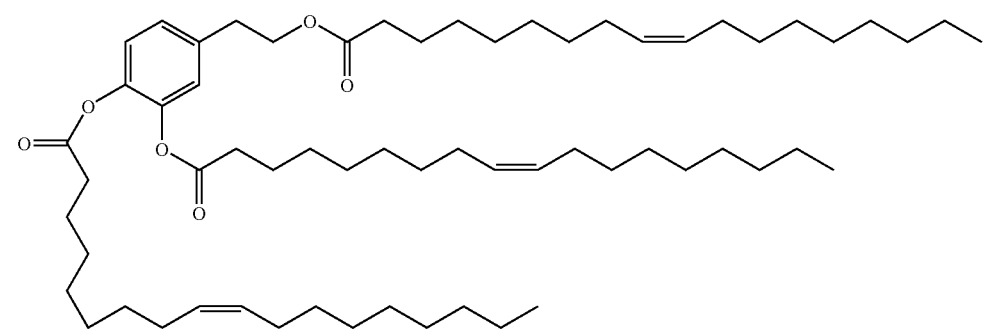
(X)
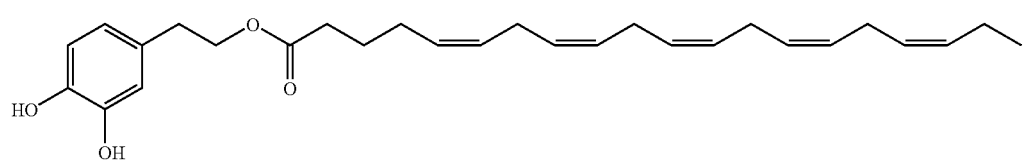
(XI)

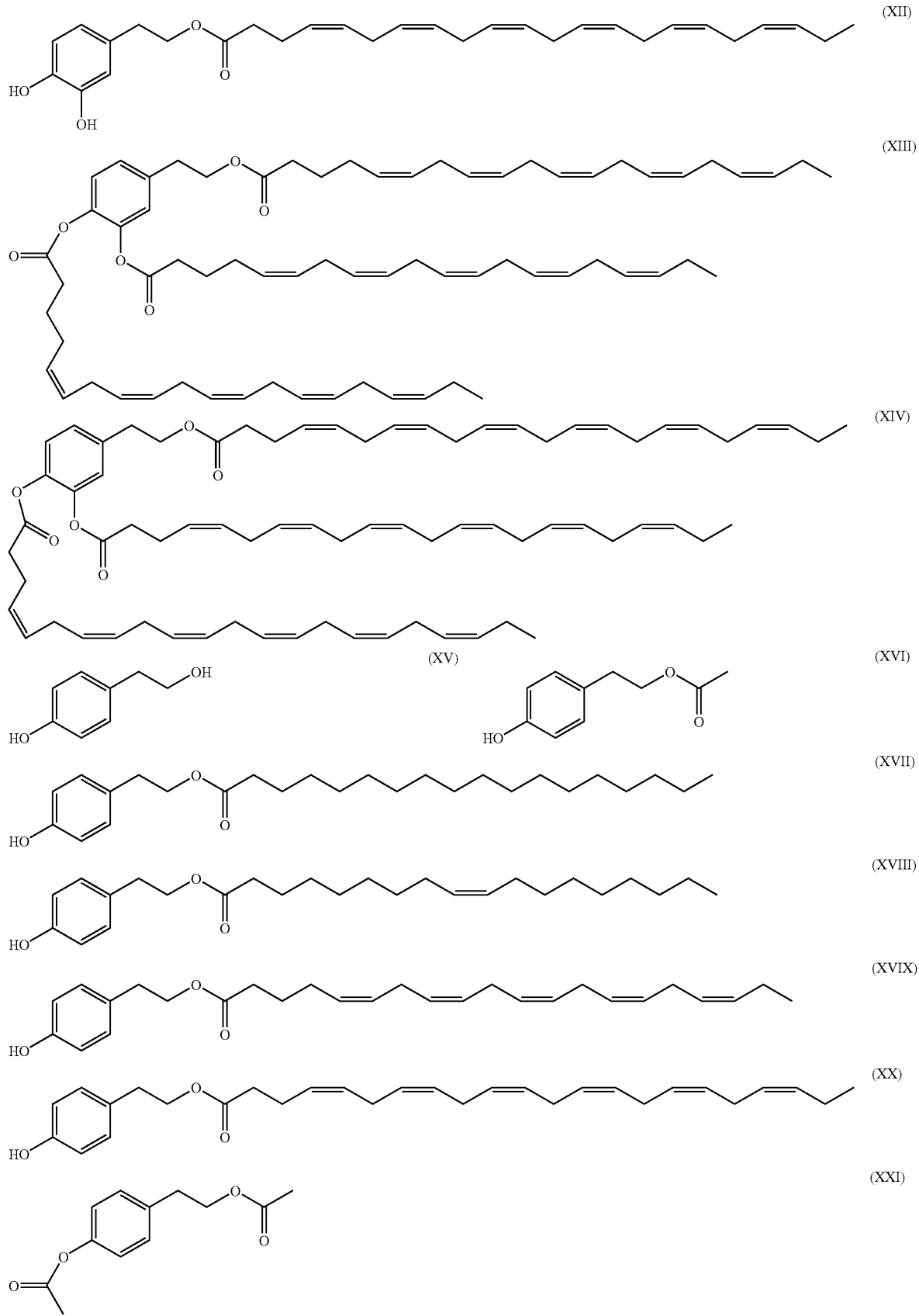

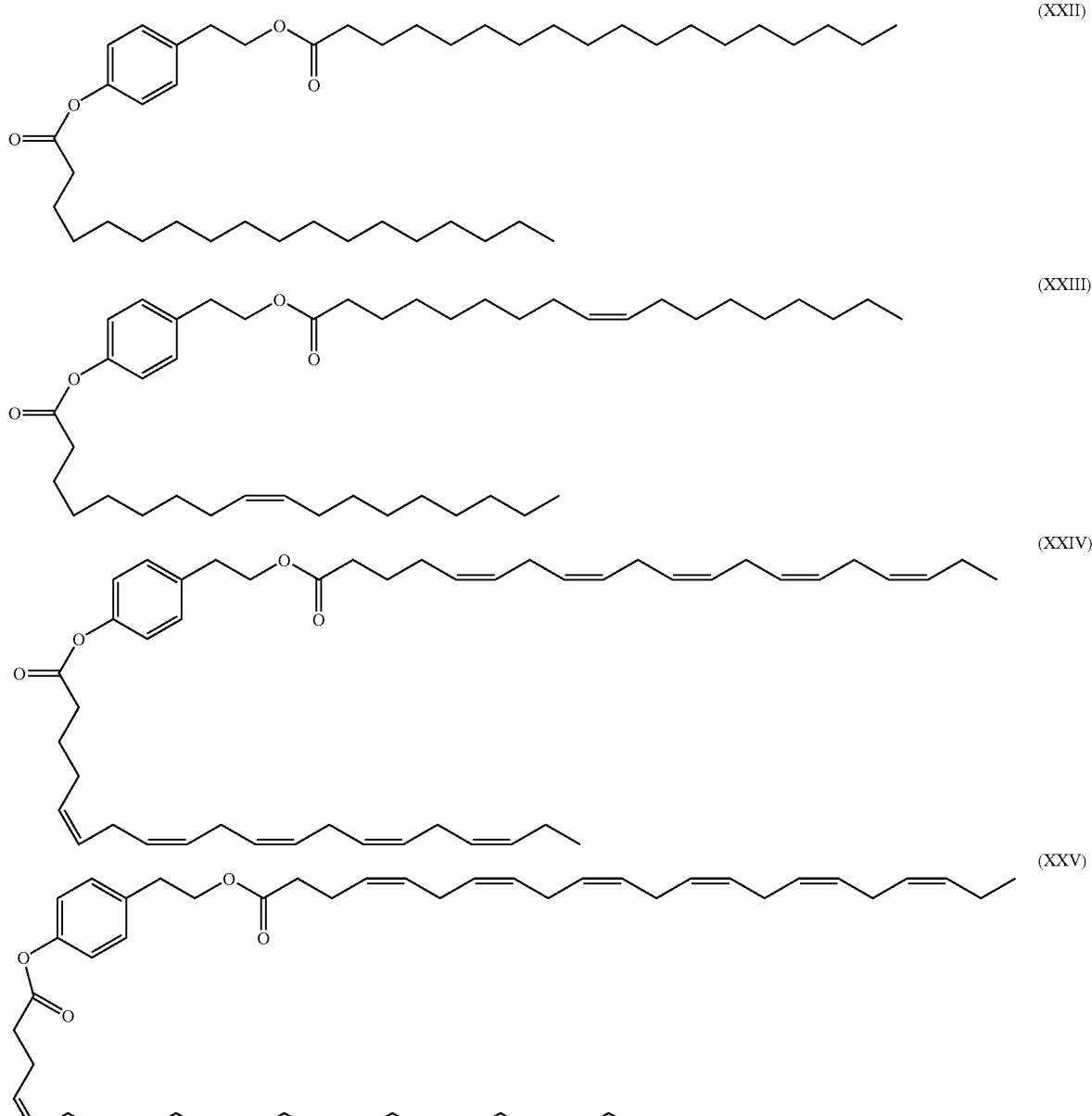

Tyrosol and hydroxytyrosol are good candidates for use in the prevention and treatment of acute and chronic cardiovascular, hepatic, renal and inflammatory diseases either as drugs or as food ingredients, since they effectively combat oxidative stress and, hence, the production of proinflammatory substances and the recruitment of cells involved in these processes. But two problems arise concerning their use as antioxidants to prevent these diseases:

1) They can be oxidised in the food matrix or in the pharmaceutical formulation.

2) The solubility of tyrosol and hydroxytyrosol in food products with a high fat composition.

This invention presents tyrosol and hydroxytyrosol derivatives that find a way around both these problems. The tyrosol and hydroxytyrosol groups in the new derivatives are partially or completely protected against oxidation. When tyrosol or hydroxytyrosol esters are compared with tyrosol or hydroxytyrosol, the esters are much more stable against oxidation.

Also, the solubility of these esterified derivatives can be modulated depending on the fatty acid chain length and the number of chains that the tyrosol or hydroxytyrosol molecules esterify. A range of solubilities can be obtained, from compounds completely soluble in the aqueous phase, for example using acetic acid to form a hydroxytyrosol ester protecting only one of the hydroxyl groups, to compounds that are completely soluble in the fatty phase, for example, using oleic acid to form a hydroxytyrosol ester.

Moreover, the inclusion of the new tyrosol and hydroxytyrosol derivatives in liposomes is disclosed. This protects these compounds from oxidation, and from the presence of metals that can cause their degradation and make them useless as antioxidants. The liposomes may be incorporated into food products with either a majority aqueous or oily phase.

The new tyrosol and hydroxytyrosol derivatives are hydrolysed in the intestinal tract of mice into the two components, tyrosol or hydroxytyrosol, and the corresponding fatty acid. After that, the two molecules are rapidly absorbed by the organism and detected in the plasma. After their absorption, both compounds can act as antioxidants to prevent diseases related with oxidative stress and inflammatory diseases.

The following examples illustrate the invention:

EXAMPLE 1

Preparation of 2-(3,4-dihydroxyphenyl) ethyl acetate (III)

To a solution of 2-(3,4-dihydroxyphenyl) ethanol (100 mg, 0.65 mmol) in dry THF (5 ml), anhydrous $K_2CO_3$ (90 mg, 0.65 mmol), acetyl chloride (0.46 ml, 0.66 mmol) and tetrabutylammonium hydrogen sulphate (TBAH) (22 mg, 0.06 mmol) were added. The mixture was shaken under argon at room temperature for 15 h, then filtered and evaporated to dryness. The residue was dissolved in dichloromethane (50 ml), washed with water (2×50 ml) and the organic phase was dried with anhydrous sodium sulphate, filtered and evaporated to dryness. The residue was purified by column chromatography using an hexane-ethyl ether mixture (1:1) as an eluent to obtain 72 mg (57%) of compound III as a transparent syrup.

RMN-$^1$H (300 mHz, $CDCl_3$): 6.78 (d, J=8.1 Hz, 1H, aromatic), 6.73 (d, J=1.5 Hz, 1H, aromatic), 6.63 (dd, J=8.0, 1.5 Hz, 1H, aromatic), 4.23 (t, J=7.1 Hz, 2H, —$CH_2$OOC—), 2.81 (t, J=7.1 Hz, 2H, ar-$CH_2$—), 2.03 (s, 3H, —$CH_3$)

Preparation of 2-(3,4-dihydroxyphenyl) ethyl stearate (IV)

To a solution of 2-(3,4-dihydroxyphenyl)ethanol (100 mg, 0.65 mmol) in dry THF (5 ml) anhydrous $K_2CO_3$ (90 mg, 0.65 mmol), stearyl chloride (197 mg, 0.66 mmol) and 22 mg of tetrabutylammonium hydrogen sulphate (TBAH) were added. The mixture was shaken under argon at room temperature for 24 h then filtered and evaporated to dryness. The residue was dissolved in dichloromethane (50 ml), washed with water (2×50 ml) and the organic phase dried with anhydrous sodium sulphate, filtered and evaporated to dryness. The residue was purified by column chromatography using an hexane-ethyl ether mixture (2:1) to obtain 132 mg (48%) of compound IV as a white solid.

RMN-$^1$H (300 mHz, $CDCl_3$): 6.79 (d, J=8.1 Hz, 1H, aromatic), 6.72 (d, J=2, 1H, aromatic), 6.63 (dd, J=8.0, 2.0 Hz, 1H, aromatic), 4.23 (t, J=7.1 Hz, 2H, —$CH_2$OOC—), 2.80 (t, J=7.1 Hz, 2H, ar-$CH_2$—), 2.28 (t, J=7.4 Hz, 2H, —OOC—$CH_2$—), 1.58 (m, 2H, —OOC—$CH_2$—$CH_2$—), 1.24 (m, 28H, —$CH_2$—), 0.87 (t, J=6.9, 3H, —$CH_3$).

Preparation of 2-(3,4-dihydroxyphenyl) ethyl oleate (V)

To a solution of 2-(3,4-dihydroxyphenyl)ethanol (100 mg, 0.65 mmol) in dry THF (5 ml), anhydrous $K_2CO_3$ (90 mg, 0.65 mmol), oleyl chloride (0.27 ml, 0.75 mmol) and tetrabutylammonium hydrogen sulphate (TBAH) were added. The mixture was shaken under argon at room temperature for 24 h, then filtered and evaporated to dryness. The residue was dissolved in dichloromethane (50 ml), washed with water (2×50 ml) and the organic phase was dried with anhydrous sodium sulphate, filtered and evaporated to dryness. The residue was purified by column chromatography using an hexane-ethyl ether mixture (4:1) as an eluent to obtain 128 mg (47%) of compound V as a slightly yellowish syrup.

RMN-$^1$H (300 mHz, $CDCl_3$): 6.78 (d, J=8.1 Hz, 1H, aromatic), 6.72 (d, J=2, 1H, aromatic), 6.63 (dd, J=8.0, 2.0 Hz, 1H, aromatic), 5.34 (m, 2H, HC=CH), 4.23 (t, J=7.1 Hz, 2H, —$CH_2$OOC—), 2.80 (t, J=7.1 Hz, 2H, ar-$CH_2$—), 2.28 (t, J=7.6 Hz, 2H, —OOC—$CH_2$—), 1.99 (m, 4H, —C$\underline{H}_2$—HC=CH—C$\underline{H}_2$—), 1.58 (m, 2H, —OOC—$CH_2$—C$\underline{H}_2$—), 1.26 (m, 26H, —$CH_2$—), 0.87 (t, J=6.9, 3H, —$CH_3$).

Preparation of 2-(3,4-monostearoyloxyphenyl) ethanol. (VI and VII)

To a solution of 2-(3,4-dihydroxyphenyl)ethanol (80 mg, 0.52 mmol) in dry THF (5 ml), pyridine (0.06 ml) and stearic anhydride (290 mg, 0.53 mmol) were added. The mixture was shaken for 24 h in an inert atmosphere at room temperature. Next, the pyridine residues were removed by coevaporating with toluene (3×25 ml) and the residue was evaporated to dryness. The residue was dissolved in dichloromethane (50 ml), washed with water (2×50 ml), dried over anhydrous sodium sulphate and the organic phase was concentrated to dryness. The residue was purified by column chromatography using a chloroform-methanol mixture 20:1 as the mobile phase to obtain 44 mg (20%) of a white solid that was found to be a (1:1) mixture of compounds VI and VII.

RMN-$^1$H of the 1:1 mixture of compounds VI and VII (300 mHz, $CDCl_3$): 7.00 (d, J=8.1 Hz, 1H, aromatic), 6.96 (dd, J=5.3, 2.1 Hz, 2H, aromatic), 6.95 (s, 1H, aromatic), 6.87 (d, J=2.1 Hz, 1H, aromatic), 6.77 (dd, J=8.2, J=2.1 Hz, 1H, aromatic), 3.83 (t, J=6.4 Hz, 2H, —$CH_2$OH), 3.82 (t, J=6.4 Hz, 2H, —$CH_2$OH), 2.80 (t, J=6.4 Hz, 2H, -ar-$CH_2$—), 2.78 (t, J=6.4 Hz, 2H, -ar-$CH_2$—), 2.59 (t, J=7.4 Hz, 4H, -ar-OOC—$CH_2$—), 1.75 (m, 4H, -ar-OOC—$CH_2$—C$\underline{H}_2$—), 1.25 (m, 56H, —$CH_2$—), 0.87 (t, J=6.9 Hz, 6H, —$CH_3$).

Preparation of 2-(3,4-diacetoxyphenyl) ethyl acetate (VIII)

To a solution of 2-(3,4-dihydroxyphenyl) ethanol (200 mg, 1.3 mmol) in dry THF (10 ml), pyridine (0.5 ml), acetic anhydride (0.6 ml) and 4-dimethylaminopyrridine (30 mg) were added. The reaction mixture was shaken under argon for 7 h at room temperature. Next, methanol (25 ml) was added and the mixture was coevaporated with toluene (3×10 ml) to dryness. The product obtained was purified by column chromatography using an hexane-ethyl ether mixture (1:1) as an eluent to obtain 136 mg (75%) of compound VIII as a syrup.

RMN-$^1$H— (300 mHz, $CDCl_3$): 7.10 (dd, J=10.2, 1.9 Hz, 2H, aromatic), 7.04 (s, 1H, aromatic), 4.26 (t, J=6.9 Hz, 2H, —$CH_2$OOC—), 2.89 (t, J=6.9 Hz, 2H ar-$CH_2$—), 2.27 (s, 3H, -ar-OCOC$H_3$), 2.26 (s, 3H, -ar-OCOC$H_3$), 2.02 (s, 3H, —$CH_2$—OCOC$\underline{H}_3$).

Preparation of 2-(3,4-distearyloxyphenyl) ethyl stearate (IX)

To a solution of 2-(3,4-dihidroxyphenyl) ethanol (100 mg, 0.65 mmol) in dry THF (10 ml) shaking at 0° C., stearic acid (563 mg, 1.98 mmol), dicyclohexylcarbodiimide (410 mg, 1.98 mmol) and 4-dimethylaminopyrridine (25 mg, 0.19 mmol) were added. The reaction mixture was shaken under argon for 24 h at room temperature. Next, the precipitated urea was filtered and the filtrate was evaporated to dryness. The residue was dissolved in dichloromethane (25 ml), washed twice with 0.5 N HCl (2×50 ml), with a saturated solution of $NaHCO_3$ and with a saturated solution of sodium chloride (1×50 ml). The combined organic phases were dried with anhydrous sodium sulphate, filtered and evaporated to dryness. The product obtained was purified by column chromatography using an hexane-ethyl ether mixture (6:1) as an eluent to obtain 200 mg (32%) of compound IX as a white solid.

RMN-$^1$H (300 mHz, $CDCl_3$): 7.08 (m, system AB, 2H aromatic), 7.02 (s, 1H, aromatic), 4.26 (t, J=7.0 Hz, —$CH_2$OOC—), 2.91 (t, J=7.0 Hz, 2H, ar-$CH_2$—), 2.50 (t, J=7.5 Hz, 4H, ar-OOC—$CH_2$—), 2.26 (t, J=7.5 Hz, 2H, —OOC—$CH_2$—), 1.71 (m, 4H, -ar-OOC—$CH_2$—$CH_2$—), 1.62 (m, 2H, —OOC—$CH_2$— $CH_2$—), 1.24 (m, 84H —$CH_2$—), 0.87 (t, J=6.9 Hz, 9H, —$CH_3$).

EXAMPLE 2

Stability against Oxidation of 2-(3,4-dihydroxyphenyl) ethyl acetate (III), 2-(3,4-diacetoxyphenyl) ethyl acetate (VIII) and hydroxytyrosol (II) when these are Incorporated in an Oily Food Matrix The stability against oxidation of II, III and VIII dissolved in refined oil was studied. This was done by measuring the remaining amount of each of the compounds when these were subjected to forced oxidation at 120° C. Oxidation was done by passing a dry air current (~20 l/h) through an aliquot of the sample (4 ml) placed in a reactor heated to 120° C. using a Metrohm-Herisau A. G Rancimat apparatus.

The solutions of all the compounds were prepared in refined oil. A total of 5 mg of II were dissolved in 5 g of refined oil, and finally 0.5 g of this solution were dissolved in. 5 g of refined oil. Similarly, solutions III and VIII were prepared in refined oil. Aliquots of 0.3 ml were collected at different times for each solution and were stored at –20° C. Isolation of compounds II and III from refined oil was done using solid phase extraction (cartridge of diol phase) with a preconditioned process of 6 ml of methanol and 6 ml of hexane. After introducing the sample, 6 ml of hexane, 6 ml of hexane/ethyl acetate (9:1) and 10 ml of methanol were passed through it, and then the methanolic fraction was concentrated to 1 ml volume. Compound VIII was also isolated using solid phase extraction with LC-Diol cartridge, with the same preconditioned process, and 12 ml of hexane and 10 ml of methanol were passed through the mixture. Once again, the methanolic phase was concentrated to 1 ml volume for analysis. Analysis and quantification of II, III and VIII was carried out by reverse-phase high performance liquid chromatography (RP-HPLC) with UV detection at 254 and 280 nM. FIG. 1 shows the remaining amount of compounds II, III and VIII at different temperatures during forced oxidation at 120° C.

It can be clearly observed in FIG. 1 that the mono-acetylated compound (III) takes longer to degrade than hydroxytyrosol (II), and therefore hydroxytyrosol in this acetylated form is better conserved in the food matrix than when its ester group is not modified. This effect is much clearer in the case of the tri-acetylated compound (VII), where 50% of the compound remains even after 10 hours whereas compounds II and III have completely degraded.

EXAMPLE 3

Absorption of Hydroxytyrosol (II) Administered Orally in Human Volunteers

Experimental Design and Methods.

Pure hydroxytyrosol was obtained from olive leaves using standard extraction procedures compatible with the consumption of food products.

A 2.5 mg dose of hydroxytyrosol was administered per kg weight to 5 fasting healthy volunteers aged from 22–30 years who had not taken olive oil in their diet for at least two days before the study. Hydroxytyrosol dissolved in water was administered orally and afterwards blood samples were obtained at 0, 10, 20, 30, 60, 120 minutes. The plasma level of hydroxytyrosol and derived metabolites were determined by gas chromatography-mass spectometry using anthracene and napthol as internal standards.

Results

The results of the study are shown in FIG. 2. In plasma the following compounds were identified: hydroxytyrosol (3,4 dihydroxyphenylethanol) and its metabolite derivative, vanillic acid (4-hydroxy-3-methoxy-phenylacetic acid), probably resulting from the activity of the enzyme catechol orthomethyl transferase on hydroxytyrosol. Neither homovanillic alcohol or aldehyde were found in the plasma samples. Hydroxytyrosol absorption was done rapidly since the maximum plasma level was detected 10 minutes after administration, returning to values similar to initial ones after 30 minutes. On the other hand, homovanillic acid starts being detectable in the plasma at significant levels 10 minutes after administering hydroxytyrosol and showed an absorption peak 30 minutes after administration of the solution. It is also interesting to note that homovanillic acid disappears from the plasma more slowly than hydroxytyrosol.

In conclusion, according to the absorption study, hydroxytyrosol 1) is absorbed rapidly in the intestine, 2) is bioavailable at least 30 minutes after its administration and 3) is metabolised rapidly to homovanillic acid.

EXAMPLE 4

Absorption of Hydroxytyrosol (II) and Hydroxytyrosol Derivatives III and IX Administered Orally in Mice The absorption in rats of hydroxytyrosol (II), (II), 2-(3, 4-dihydroxyphenyl) ethyl acetate (III), also called hydroxytyrosol acetate and 2-(3,4-distearyloxyphenyl) ethyl stearate (IX), also called hydroxytyrosol tristearate was studied. For this purpose, oily solutions of equivalent amounts of each compound were prepared (10 mg of II, 13 mg of III and 70 mg of IX) to be administered orally to mice from which blood samples were collected after 15 and 60 minutes. Plasma was isolated from each blood sample by extraction with ethyl acetate and analysed by gas chromatography-mass spectometry. The amounts of hydroxytyrosol detected in plasma after oral administration of compounds II and III were very similar (see Table below)

| Compound administered | Hydroxytyrosol in plasma, 15 min. | Hydroxytyrosol in plasma, 60 min. |
|---|---|---|
| Hydroxytyrosol (II) | 0.79 mg/l | 0.05 mg/l |
| 2-(3,4-dihidroxyphenyl) ethyl acetate (III) | 0.68 mg/l | 0.06 mg/l |
| 2-(3,4-distearyloxyphenyl) ethyl stearate (IX) | not detected | 0.44 mg/l |

When 2-(3,4-distearyloxyphenyl) ethyl stearate (IX) was administered to mice, only hydroxytyrosol (II) was detected in plasma 1 hour after administration, since after 15 minutes hydroxytyrosol was not detected in plasma (see table above). These results indicate that, although at different rates, both 2-(3,4-dihydroxyphenyl) ethyl acetate (III), and 2-(3,4-distearyloxyphenyl) ethyl stearate (IX), release hydroxytyrosol in the stomach or intestine of mice after which this can be absorbed and pass to the blood stream.

EXAMPLE 5

Preparation of an Enriched Juice

A juice was prepared enriched in the following ingredients:

| Ingredient | Amount per kg | |
|---|---|---|
| Concentrated juice | 200 | g |
| 2-(3,4-dihydroxyphenyl) ethyl acetate | 1 | g |
| Insoluble fibre | 10 | g |
| Lecithin | 0.5 | g |
| Flavors | 2 | g |
| Vitamin C | 90 | mg |
| Vitamin B1 | 2.1 | mg |
| Vitamin B2 | 2.4 | mg |
| Vitamin B6 | 3 | mg |
| Vitamin B12 | 1.5 | μg |
| Vitamin A | 1.2 | mg |
| Vitamin D | 7.5 | μg |
| Folic acid | 300 | μg |

Procedure

The final product was prepared by adding water and the water-soluble ingredients to the juice concentrate. Next, 2-(3,4-dihydroxyphenyl) ethyl acetate was added, the mixture was suitably blended and the resulting product pasteurised and homogenised. Finally, the product was left to cool and then packaged.

EXAMPLE 6

Preparation of a Product Based on UHT Milk

A product was prepared based on UHT milk with the following ingredients:

| Ingredient | Amount per litre | |
|---|---|---|
| Skimmed milk | 960 | g |
| Powdered skimmed milk | 17 | g |
| 2-(3,4-dihydroxyphenyl) ethyl acetate | 1 | g |
| Bisodium phosphate | 0.5 | g |
| Tripotassium phosphate | 0.2 | g |
| Water | 2 | g |
| Vitamin B6 | 3 | mg |
| Vitamin B12 | 3.8 | μg |
| Vitamin A | 1200 | μg |
| Vitamin D | 7.5 | μg |
| Vitamin E | 15 | mg |
| Folic acid | 300 | μg |

Procedure

The solid ingredients were combined with the liquid milk and water. Next, hydroxytyrosol acetate was added and the mixture was homogenised in the absence of oxygen. The resulting milk product was submitted to a UHT treatment (150° C. for 4–6 seconds) and finally packaged in the absence of oxygen.

EXAMPLE 7

Preparation of a Drink with a Nutritionally Balanced Formula

A drink was prepared with a nutritionally balanced formula with the following ingredients:

| Ingredients | Amount per litre | |
|---|---|---|
| Skimmed milk | 814.3 | g |
| Serum protein concentrate | 11.8 | g |
| Mixture of oils | 32.5 | g |
| Sucrose | 27 | g |
| Maltodextrin | 71 | g |
| Soluble fibre | 10 | g |
| Vitamin A | 1200 | mg |
| Vitamin D | 7.5 | μg |
| Vitamin E | 15 | mg |
| Vitamin K | 120 | μg |
| Vitamin C | 90 | mg |
| Thiamin | 2.25 | mg |
| Riboflavin | 2.55 | mg |
| Pyridoxine | 3 | mg |
| Vitamin B12 | 3 | μg |
| Niacin | 28.5 | mg |
| Folic acid | 30 | μg |
| Pantothenic acid | 4 | mg |
| Biotin | 40 | μg |
| Calcium | 1200 | mg |
| Phosphorus | 970 | mg |
| Magnesium | 47 | mg |
| Sodium | 480 | mg |
| Potassium | 1000 | mg |
| Chloride | 700 | mg |
| Iron | 43 | mg |
| Zinc | 24.5 | mg |
| Iodine | 150 | μg |
| Manganese | 100 | μg |
| Selenium | 10 | μg |
| Mono- and diglycerides | 1.5 | g |
| Bisodium phosphate (Na$_2$HPO$_4$) | 0.6 | g |
| Carragenates | 4 | g |
| Demineralised water | 70 | g |
| Flavors | 2.75 | g |
| 2-(3,4-dihydroxyphenyl)ethyl acetate | 1.5 | g |

Procedure

All the solid ingredients were combined with the liquid milk and the water in a tank provided with suitable heating and stirring devices. Next, 2-(3,4-diacetoxyphenyl) ethyl acetate was added. Th mixture was heated to 60–70° C. and emulsified with a single stage homogeniser at 6–7 MPa in the absence of oxygen. After preparing the emulsion, the mixture was heated to 140–150° C., 4–6 s, and immediately afterwards passed through a two stage homogeniser (27–29 MPa and 3–4 MPa). Finally, the mixture was packaged in the absence of oxygen.

EXAMPLE 8

Preparation of a Butter Product with Antioxidant Compounds

A butter was prepared with a nutritionally balanced formula with the following ingredients:

| Ingredients | Amount per kg | |
|---|---|---|
| Butter | 200 | g |
| Mixture of oils | 208 | g |
| Starch | 8 | g |
| Casseinate | 6 | g |
| Emulsifier | 2 | g |
| Maltodextrin | 6 | g |
| Water | 570 | g |
| 2-(3,4-dihydroxyphenyl) ethyl oleate | 1.5 | g |

Procedure

First, the aqueous phase was prepared with the water-soluble ingredients. Emulsifiers and 2-(3,4-dihydroxyphenyl) ethyl oleate was dissolved in the mixture of oils. Next, the aqueous phase was incorporated in the fatty phase by continuous addition at high temperature and stirring. This mixture was pasteurised using surface heat exchangers. The final solid product was obtained by using a high-speed rotor provided with an external cooling system.

The invention claimed is:

1. A phenolic compound selected from the group consisting of 2-(3,4-dihydroxyphenyl) ethyl stearate (IV),
   2-(3,4-dihydroxyphenyl) ethyl oleate (V)
   2-(3-stearyloxy-4-hydroxyphenyl) ethanol (VI),
   2-(4-stearyloxy-3-hydroxyphenyl) ethanol (VII),
   2-(3,4-distearyloxyphenyl) ethyl stearate (IX),
   2-(3,4-dioleyloxyphneyl) ethyl oleate (X),
   2-(3,4-dihydroxyphenyl) ethyl eicosapentanoate (XI),
   2-(3,4-dihydroxyphenyl) ethyl docosahexanoate (XII),
   2-(3,4-dieicosapentanoyloxyphenyl) ethyl eicosapentanoate (XIII),
   2-(3,4-didocosahexanoyloxyphenyl) ethyl docosahexanoate (XIV),
   2-(4-hydroxyphenyl) ethyl eicosapentanoate (XIX),
   2-(4-hydroxyphenyl) ethyl docosahexanoate (XX),
   2-(4-stearyloxyphenyl) ethyl stearate (XXII),
   2-(4-oleyloxyphenyl) ethyl oleate (XXIII),
   2-(4-eicosapentanoyloxyphenyl) ethyl eicosapentanoate (XXIV), and
   2-(4-docosahexanoyloxyphenyl) ethyl docosahexanoate (XXV).

2. A pharmaceutical composition comprising a therapeutically effective amount of a compound according to claim 1 in a pharmaceutically acceptable carrier.

3. A pharmaceutical composition according to claim 2 formulated for oral administration to a patient.

4. A pharmaceutical composition according to claim 2 formulated for parenteral administration to a patient.

5. A food composition to which a therapeutically effective amount of a compound in accordance with claim 1 has been added.

6. A food composition according to claim 5 which is selected from the group consisting of milk, aromatised milk, yogurts, fermented milk products, dried milk, butter, margarine, mayonnaise, oils, sauces, bread, cakes, pastry products, biscuits, sweets, chewing gums, children's food products, dehydrated food, juices and clinical nutrition products.

7. A cosmetic composition comprising at least one of the phenolic compounds according to claim 1.

8. A cosmetic composition according to claim 7 which is a composition for solar protection.

9. A cosmetic composition according to claim 7 where the phenolic compounds are incorporated in the form of liposomes.

* * * * *